United States Patent [19]

De Vor, deceased

[11] Plant 4,665

[45] Mar. 10, 1981

[54] ROSE PLANT NAMED CHANTILLY LACE

[75] Inventor: Paul F. De Vor, deceased, late of Pleasanton, Calif., by Thelma G. De Vor, executor

[73] Assignee: De Vor Nurseries, Inc., Pleasanton, Calif.

[21] Appl. No.: 53,932

[22] Filed: Jul. 2, 1979

[51] Int. Cl.[3] ..... A01H 5/00

[52] U.S. Cl. ..... Plt./11

[58] Field of Search ..... Plt./11, 27

*Primary Examiner*—James R. Feyrer

*Attorney, Agent, or Firm*—Chas. W. Rummler

[57] ABSTRACT

A new hybrid tea rose cultivar having a vigorous and free growing habit of growth and a continuous and profuse production of large, high centered flowers of a pleasing lavender coloring and a very strong and pleasing fragrance. The flower of this variety is a two toned variety in bud shape which opens to a solid color flower when fully open and each flower is carried on a long, sturdy stem. The plant itself is free branching in growth habit with very strong, upright canes and an abundant quantity of foliage, reaching a height of more than five feet, and its flower production is year around.

1 Drawing Figure

BACKGROUND OF THE NEW PLANT

This rose cultivar is a seedling of the unpatented variety Blue Moon resulting from a cross with Angel Face (U.S. Plant Pat. No. 2,792) made by the inventor at Livermore, Calif., in the course of breeding procedures carried on with the object of producing a lavender tinted rose having a good bud and high productivity combined with the fragrance of Angel Face. This seedling was discovered by the inventor in 1972 and since it appeared to have the characteristics being sought, it was asexually reproduced by him, by budding, at Livermore, Calif., and propagated through successive generations to test its retention of the novel character first observed. Continued propagation of this cultivar at Pleasanton, Calif., and at Hamilton City, Calif., has demonstrated that its novel characteristics hold true from generation to generation and appear to be firmly fixed.

DESCRIPTION OF THE DRAWINGS

This new lavender rose cultivar is illustrated by the accompanying photographic drawings of which sheet 1 shows in FIG. 1 a full face view of a newly opened flower and in FIG. 2 shows four stages of the bloom from a bud on which the sepals have just divided to a newly opened flower in which the petals have begun to unfurl; sheet 2 shows parts of the plant including top and bottom sides of typical leaves, a newly cracked bud, a top view of a bud with the sepals fully parted, and specimens of young and mature wood; and Sheet 3 is a print of a full face view of the flower which has been hand painted to show the true colors of the flower petals.

DESCRIPTION OF THE NEW PLANT

Figure 1:
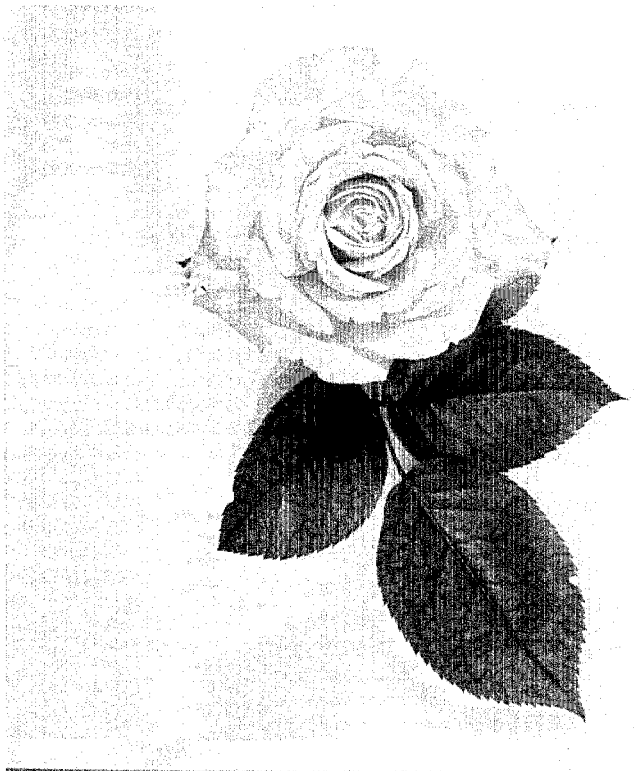
Figure 2:
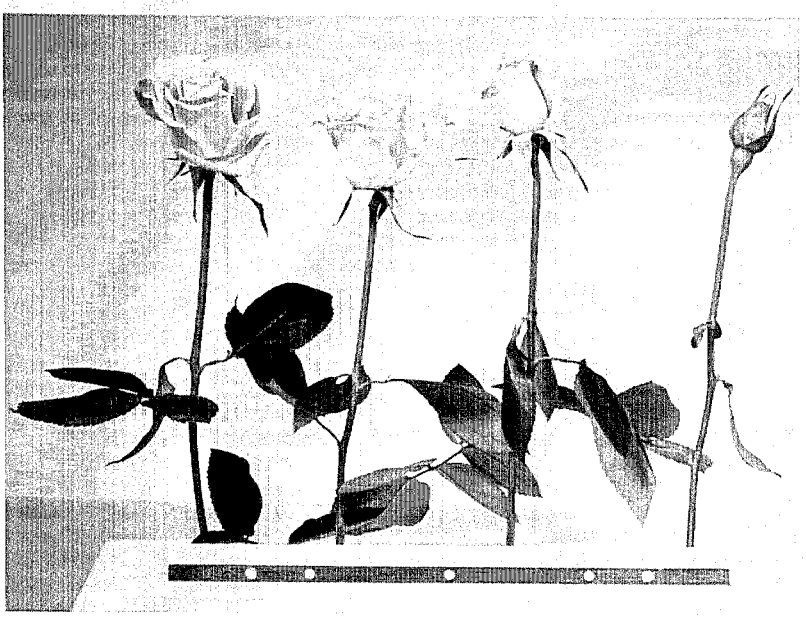
Figure 3:
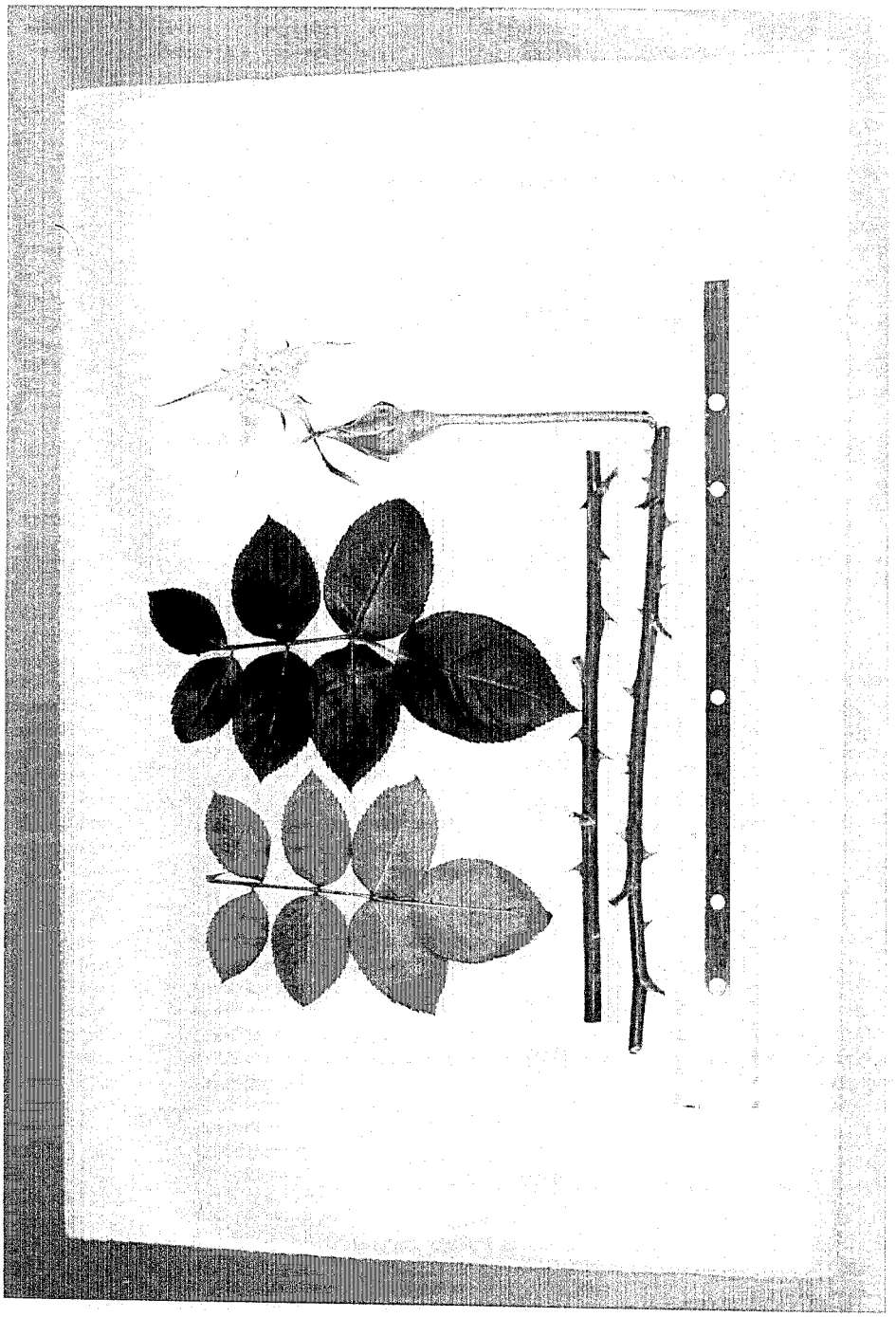

The following is a detailed description of this new rose cultivar with color designations according to The RHS Colour Chart published by the Royal Horticultural Society of London, England, in collaboration with the British Colour Council, the following data being from observation of greenhouse plants growing at Pleasanton, Calif.

THE PLANT

Origin: Seedling.

Parentage:

*Seed parent.*—Blue Moon (unpatented).

*Pollen parent.*—Angel Face (U.S. Plant Pat. No. 2,792).

Classification:

*Botanic.*—Hybrid Tea.

*Commercial.*—Greenhouse Cultivar.

Form: Upright bush.

Height: About 5 feet 4 inches.

Growth: Very strong, sturdy and vigorous.

Habit: Free branching, with strong canes and long, sturdy stems.

Foliage:

*Quantity.*—Abundant.

*Leaves.*—Number: 5 to 6, about 2 to 3 inches apart, on cut flower stem. Size: About 5 to 7½ inches long and 3¼ to 5½ inches wide. Shape: Odd pinnate. Leaflets: 3 to 7 in number. Size: Large. Shape: Ovate, with serrate margin and cuspidate apex. Color: Upper side—Green 139A. Under side—Grayed Green 191A. Texture: Smooth. Aspect: Glossy.

*Petiolule.*—1/16 to ⅛ inch long by 1/16 inch wide.

*Petioles.*—⅞ to 1½ inches long from stem, ⅜ to 1 inch long from top of auricle.

*Rachis.*—2½ to 3¾ inches long. Stipules are adnate with small hairs.

*Thorns.*—Size: About ¼ inch long and hooked slightly downward from a ¼ inch wide base. Color: Yellow Green 146D.

THE BUD

Size: About 1½ to 1¾ inches long, 1¼ inch in diameter across the center and about ⅞ inch in diameter across the base.

Shape: Urn shaped.

Color:

*When sepals first divide.*—Red Purple 66C.

*When petals begin to unfurl.*—Grayed Purple 186B.

Sepals: Spear-shaped and upstanding on the bud and curled back as the flower opens to fold downwardly along the stem.

*Color.*—Inside—Grayed Green 191B-C. Outside—Green 143A-B.

Calyx:

*Shape.*—Pear-shaped.

*Size.*—Medium-large, about ½ inch wide and ½ inch long.

*Aspect.*—Smooth.

*Splitting.*—Calyx does not split.

Peduncle:

*Length.*—About 3½ to 4¼ inches.

*Aspect.*—A very few small prickles, less than 1/16 inch long.

*Strength.*—Erect and strong, holding the flower upright. There is no tendency to nodding buds.

Color: Green 143C.

THE FLOWER

Blooming habit: Profusely and continuous the year around under glass, blooming freely in fall and winter.

Size: Large; 4 to 5 inches in diameter and 1½ inches in depth.

Borne: Singly.

Shape: High centered when the bloom first opens. The petals fold back as the bloom matures but the petaloids cover the center of the flower.

Petalage:

*Number of petals.*—33 to 35.

*Arrangement.*—Imbricated.

*Form.*—The petals are high centered and tend to curl outward when the flower is fully opened.

*Texture.*—Soft but firm and resistant to any change in form.

*Aspect.*—Satiny.

*Color.*—Outer petals: Top side—Red Purple 74C with Yellow 4A at base. Reverse side—Red Purple 63C at the margin, White 155A at the center and Yellow 10C at base. Inside petals: Top side—margin, Red Purple 66D and Yellow 4A at base. Reverse side—margin, Red Purple 62A, White 155A at center and Yellow 4A at base.

Petaloids:

*Number.*—13 to 15.

*Size.*—About ¼ to 15/16 inch long and ½ to ⅝ inch wide.

*Color.*—Red Purple 66C-66D with Yellow 4A at base.

Peduncle:

*Length.*—3½ to 4¼ inches.

*Color.*—Green 143C.

*Character.*—Sturdy and upright.

Persistence: The petals drop cleanly.

Fragrance: Strong and substantially the same as that of "Angel Face".

Lasting quality: Long lasting both on plant and as a cut flower.

REPRODUCTIVE ORGANS

Stamens:

*Anthers.*—70 to 105 in number. Arrangement: Slightly introrse. Size: 1/16 inch wide by ⅛ inch long. Color: Yellow Orange 16C.

*Filaments.*—Length: About ½ inch to ⅝ inch. Color: Green White 157A at base and Yellow White 158D near the anther.

*Pollen.*—Color: Grayed Orange 163C.

Pistils:

*Number.*—73 to 106.

*Styles.*—About ⅝ to ¾ inch long.

*Stigmas.*—Color—Grayed Yellow 160B-C.

Ovaries: Very slender and covered with silvery white hairs and the styles are unattached to each other throughout.

FRUIT

The fruit is fertile and pear-shaped in form. Its color is Orange 26A-B.

It is claimed:

1. A new and distinct variety of rose plant substantially as herein shown and described, characterized by its high-centered lavender colored blooms and very strong fragrance. This new variety has a vigorous and free growing habit of growth and a profuse year-around production of long stemmed, long lasting flowers.

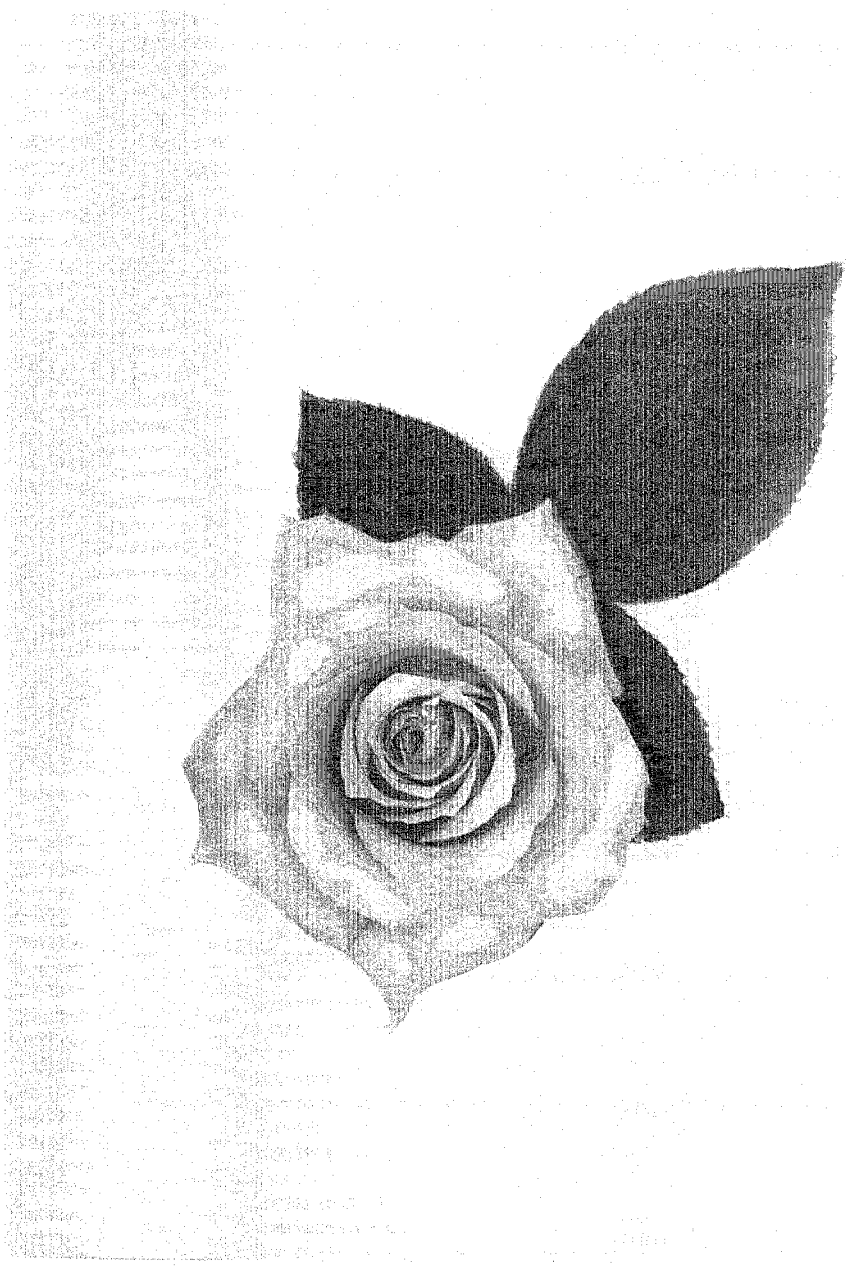

* * * * *